(12) United States Patent
King et al.

(10) Patent No.: US 6,190,547 B1
(45) Date of Patent: Feb. 20, 2001

(54) WATER TREATMENT SYSTEM

(75) Inventors: Joseph A. King, Minneapolis; Robert Edelson, Edina, both of MN (US); James Dorrans, Peoria, AZ (US)

(73) Assignee: King Technology, Inc, Hopkins, MN (US)

( * ) Notice: Under 35 U.S.C. 154(b), the term of this patent shall be extended for 0 days.

(21) Appl. No.: 09/261,787

(22) Filed: Mar. 3, 1999

Related U.S. Application Data

(63) Continuation-in-part of application No. 08/719,482, filed on Sep. 25, 1996, and a continuation-in-part of application No. 08/957,265, filed on Oct. 24, 1997.

(51) Int. Cl.[7] .................................................... C02F 1/50
(52) U.S. Cl. ...................... 210/169; 201/198.1; 201/501; 137/268; 422/261
(58) Field of Search ................................ 210/169, 198.1, 210/205, 220, 501; 252/175; 137/268; 422/261; 424/408

(56) References Cited

U.S. PATENT DOCUMENTS

| | | | |
|---|---|---|---|
| 4,642,192 | * | 2/1987 | Heskett ................................ 210/638 |
| 4,780,197 | * | 10/1988 | Schuman ............................. 210/206 |
| 5,041,219 | * | 8/1991 | Strand et al. ........................ 210/284 |
| 5,218,983 | * | 6/1993 | King ........................................ 137/1 |
| 5,251,656 | * | 10/1993 | Sexton, Sr. ............................. 137/1 |
| 5,407,567 | * | 4/1995 | Newhand ............................. 210/205 |
| 5,656,159 | * | 8/1997 | Spencer et al. ...................... 210/206 |
| 5,976,385 | * | 11/1999 | King .................................... 210/754 |
| 5,993,753 | * | 11/1999 | Davidson ............................. 210/205 |

\* cited by examiner

*Primary Examiner*—David A. Simmons
*Assistant Examiner*—Frank M. Lawrence
(74) *Attorney, Agent, or Firm*—Jacobson & Johnson

(57) ABSTRACT

Improved water treatment minerals and a canister with a divider platform for use in a dispersal valve to enable a fluid mixing stream to be bifurcated and simultaneously but separately treat the water flowing therethrough with water treatment compositions containing bacteria killing chemicals and bacteria killing minerals.

20 Claims, 12 Drawing Sheets

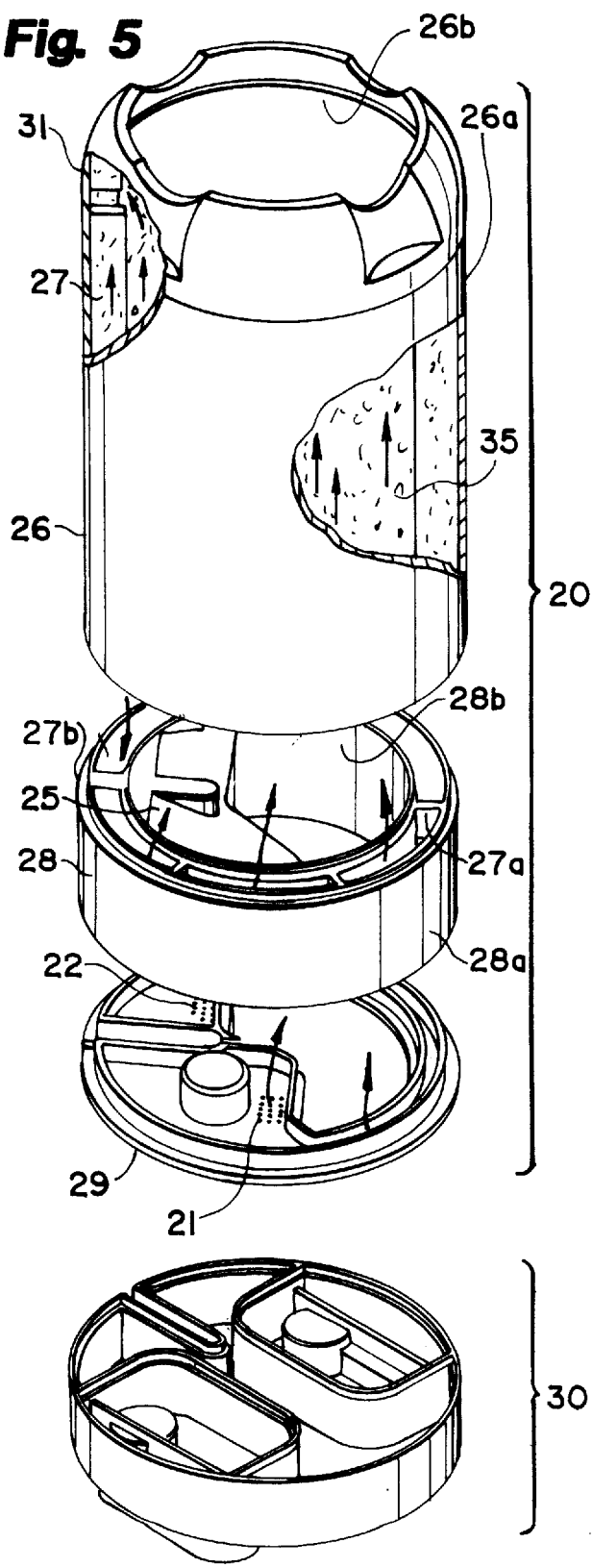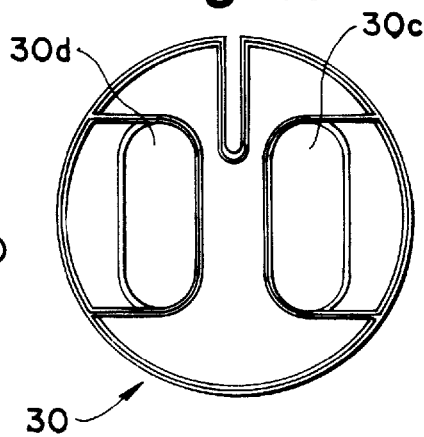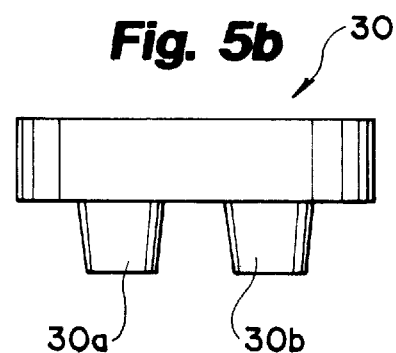

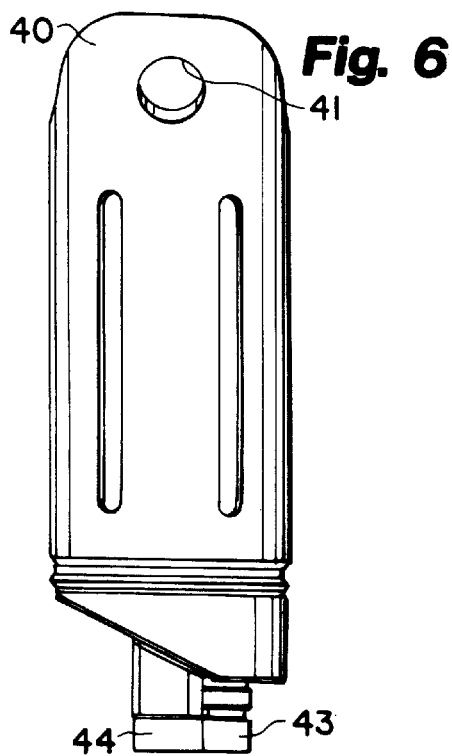
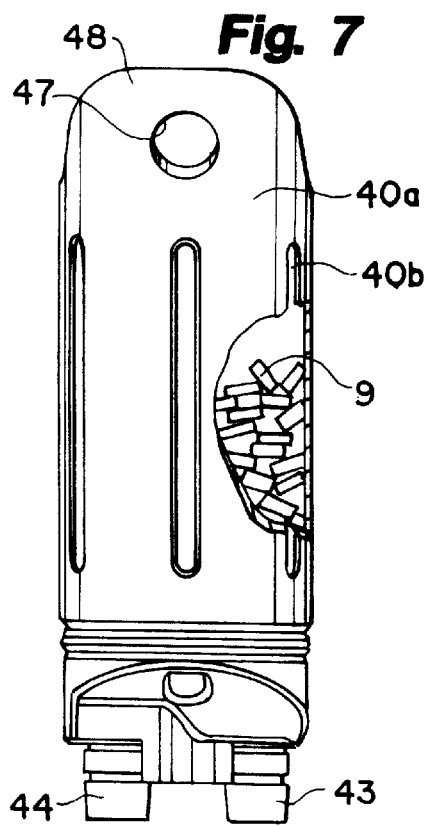
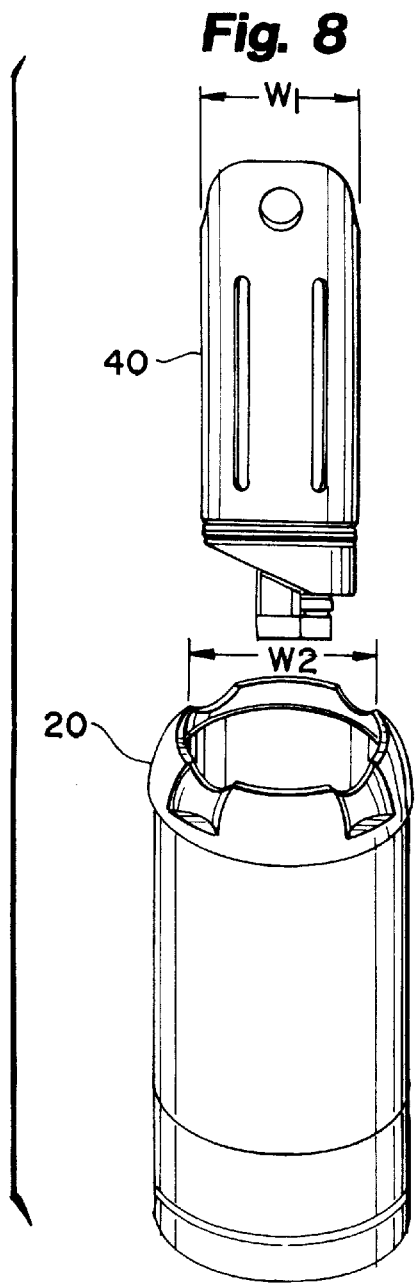

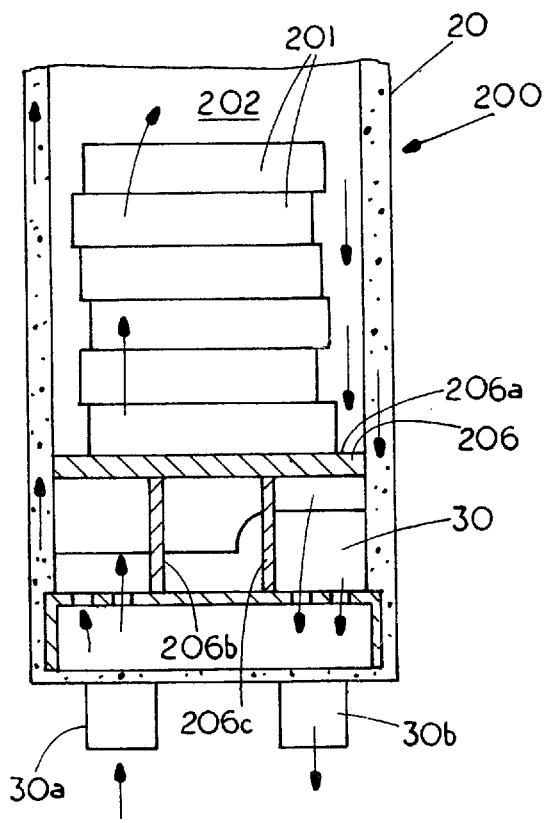
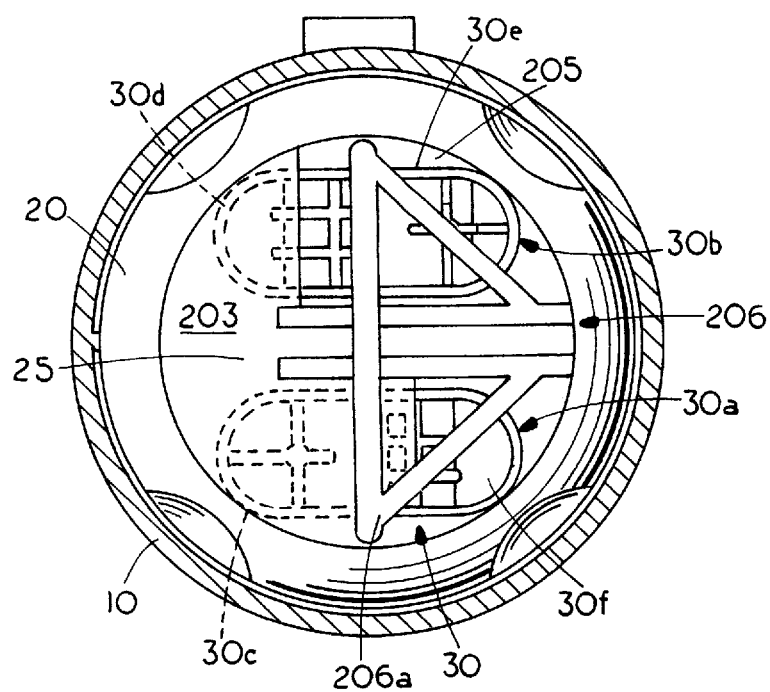

WATER TREATMENT SYSTEM

CROSS REFERENCE TO RELATED APPLICATIONS

This application is a continuation in part of co-pending U.S. patent application Ser. No. 08/719,482 titled Water Treatment Materials, filed Sep. 25, 1996, and U.S. patent application Ser. No. 08/957,265 titled Water Treatment Composition filed Oct. 24, 1997.

FIELD OF THE INVENTION

This invention relates generally to a single canister for holding and dispensing multiple dispersants including bacteria killing minerals and bacteria killing chemicals which can simultaneously but separately be dispersed to kill both bacteria and or algae in recirculating water systems commonly used in swimming pools, spas and the like and to improvements to bacteria killing minerals.

BACKGROUND OF THE INVENTION

The concept of treating water with chemicals such as chlorine or bromine to kill bacteria is old in the art. One of the methods of dispensing bacteria killing chemicals into the water is to use a dispersal valve that allows a portion of the water to flow through the water soluble chemical which is located in a single compartment within the dispersal valve. Typically, a chemical such as chlorine is used to kill the bacteria.

The prior art includes devices that hold two solids and separately dispenses the dissolvable solids into the water, such as the device shown in U.S. Pat. No. 3,378,027. The patent shows a water treatment apparatus having two separate compartments, each for holding a dissolvable solid chemical therein. Once the chemicals are dissolved they are allowed to flow into a storage tank.

Another apparatus for dispensing two different chemicals is shown in U.S. Pat. No. 5,251,656 which shows a multiple chemical feeder for swimming pools. The feeder has a first compartment for holding a canister containing a solid chemical, and a second compartment for holding a collapsible container having a liquid chemical dispersant. The solid chemical is dissolved and dispensed by the flow of water through it. The liquid chemical is dispensed by exerting pressure on the outside of a collapsible container to force the liquid chemical out of the dispenser and into the system. The chemicals are maintained separately from one another until they are introduced into the fluid stream. In the present invention, one portion of a bifurcated fluid stream flows through a chemical dispersant, such as chlorine, and the other portion flows through bacteria killing minerals to provide a system where the levels of the chemical dispersants can be maintained at a lower level than if chemicals were solely relied upon to maintain a low bacteria level. The advantage of using a lower level of chemicals is the corresponding reduction in chlorine smell. After passing through the canisters, the bifurcated stream is reunited and then directed into the liquid stream flowing through the dispersal valve.

The invention allows one to use a prior art single compartment dispersal valve to hold a single canister wherein two different materials can be separately dissolved and simultaneously dispersed into a bifurcated fluid mixing stream with the bifurcated fluid mixing steam subsequently combined into a single stream for delivering the chemical and mineral dispersants into the liquid stream through a single dispersal valve.

In one embodiment two canisters are employed to dispense both the bacteria killing chemicals and the bacteria killing mineral, and in another embodiment only a single canister is used to dispense both the bacteria killing chemicals and the bacteria killing minerals.

The invention further includes improved bacteria killing minerals which can be used in the dispersal valve. One improved bacteria killing mineral comprises zinc metal particles and a limestone carrier with at least some of the limestone having a silver chloride coating thereon. A further improved bacteria killing mineral comprises zinc metal particles having a coating of silver chloride with a further coating of porous epoxy thereon. The zinc, silver and silver chloride are believed to yield ions that inhibit bacteria and algae, while the limestone neutralizes acids formed during the water treatment process. The combination of a water chemical treatment and a mineral treatment provides a treatment system that lowers the necessary amount of chemical in the water. A suitable bacteria killing mineral for use in the single canister with two compartments comprises zinc metal particles with a portion of the zinc metal particles covered with either silver metal or silver chloride.

An adhesive is used to secure the limestone and the silver chloride or the zinc and the silver chloride. By forming the adhesive in a matrix, one can maintain both bacteria killing minerals and the bacteria killing chemical in a reactive state.

Although an adhesive is described, a mechanical restraint or other mechanism for maintaining the minerals in fluid proximity to one another can be used.

BRIEF DESCRIPTION OF THE PRIOR ART

U.S. Pat. No. 3,378,027 shows a water treatment apparatus having two separate compartments each for holding dissolvable chemicals therein. Once the chemicals are dissolved with water, the dissolvable chemicals are allowed to flow into a storage tank.

U.S. Pat. No. 4,504,387 shows a water purification system that uses charcoal granules impregnated with silver ions to kill bacteria.

U.S. Pat. No. 4,608,247 discloses a composition for bacterial treatment of water that uses a combination of a carrier with a layer of elemental silver on the carrier. The silver is released by the mechanical interaction of adjacent particles. The silver and carrier are located in a filler material that reduces the rate of release of the silver into the fluid stream.

U.S. Pat. No. 4,610,783 shows a system for the control of algae where the water is forced through staggered holes located in a set of zinc disks.

U.S. Pat. No. 4,642,192 shows a method for treating fluid to remove dissolved chlorine and nitrates by passing the water through a metal particulate matter such as aluminum, iron, steel, zinc, copper or mixtures and alloys thereof.

U.S. Pat. No. 4,662,387 discloses an inline dispersal valve with a canister keyed to the dispersal valve.

U.S. Pat. No. 4,867,196 shows a dispenser with three chambers to obtain uniform and controlled release of the calcium hypochlorite.

U.S. Pat. No. 4,935,116 shows a canister that contains two dissimilar metals that are spaced from one another with one of the metals being silver to produce a simple voltaic cell that release silver ions into the water as the water flows between the two dissimilar metals.

U.S. Pat. No. 4,964,185 shows a system for dispensing a chemical into a fluid stream and for determining how much of the chemical has been dispensed into the fluid stream.

U.S. Pat. No. 5,041,219 discloses a dual chamber water filter with a metallic filtration particulate located in the inlet chamber and a charcoal filtration particulate located in the outlet chamber with the metallic filtration particulate positioned so that water flows upward through it to reduce compaction of the metallic filtration particulate.

U.S. Pat. No. 5,218,983 and King U.S. Pat. No. 5,076,315 disclose a dispersal valve with a canister for dispensing a water soluble chemical into a fluid stream.

U.S. Pat. No. 5,251,656 shows a multiple chemical feeder for swimming pools that has a first compartment for holding a canister containing a solid chemical and a second compartment containing a liquid chemical. The solid chemical is dissolved by the flow of water through it. The liquid chemical is dispensed by exerting pressure on the outside of a collapsible container to force the liquid chemical out of the dispenser and into the system.

U.S. Pat. No. 5,352,369 discloses a method of treating water to kill bacteria using a silver catalyst which comprises and aluminum matrix with silver deposited thereon, and the aluminum matrix and the silver having been heated between 750° C. and 1050° C.

U.S. Pat. No. 2,107,456 discloses a portable water treating system having a bed of germicidal filter material that has activated carbon filter stacked on the germicidal filter materiel.

U.S. Pat. No. 4,092,245 shows a liquid purification system using biocatalysts formed by wet processing silver oxide, zinc oxide and lampblack.

U.S. Pat. No. 4,407,865 discloses a process of coating a sterilizing filter material comprised of particulate silver material such as sand with metallic silver for sterilizing water.

BRIEF DESCRIPTION OF THE INVENTION

Briefly, the present invention comprises a water treatment system for delivering bacteria killing minerals and improved bacteria killing minerals with the water treatment system including a single canister having an internal annular chamber to dispense a bacteria killing mineral and a second external chamber to support dispense a free-sitting bacteria killing chemical so that a dispersal valve can bring the water in a system into contact with both bacteria killing minerals and the bacteria killing chemicals. The single canister permits simultaneous but separate treatment of a temporarily bifurcated fluid mixing stream flowing through a set of dispersal valve ports.

BRIEF DESCRIPTION OF THE DRAWINGS

FIG. 5 is an exploded view of the nestable canister of FIG. 4 together with a manifold for connecting the nestable canister to a dispersal valve;

FIG. 5A is a top view of the manifold of FIG. 4;

FIG. 5B is front view of the manifold of FIG. 4;

FIG. 6 is a front view of a second nestable canister for nesting within the canister of FIG. 4;

FIG. 7 is a partial cut-away side view of a second nestable canister of FIG. 6;

FIG. 8 is an exploded perspective view showing the nesting relationship of the nestable canisters of FIG. 4 and FIG. 6;

FIG. 15 is a cross-sectional view of the canister of FIG. 14 holding a stack of bacteria killing chemicals therein;

FIG. 16 is a top view of the canister of FIG. 14 showing the bottom of the canister with a platform support therein for holding the stack of bacteria killing chemicals in a stacked arrangement;

DESCRIPTION OF THE PREFERRED EMBODIMENTS

Figure 2:
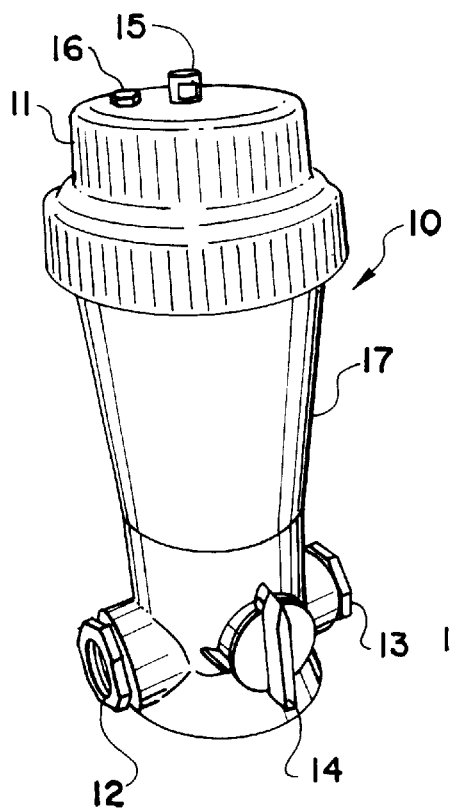
FIG. 2 is a pictorial view of a prior art dispersal valve.

FIG. 2 reference numeral 10 general identifies a prior art dispersal valve for normally and controllable dispersing a single solid dispersant chemical such as bromine or chlorine tablets into a liquid. Dispersal valve 10 includes a housing 17 having a removable cover 11 fastened thereto by threads or the like. Located on top of cover 11 is an air vent 16 that can be opened to bleed air from dispersal valve 10. Located on top center of cover 11 is a visual indicator means 15 comprising an outer transparent, hollow sight member that permits an observer to peer through the sight member to determine if a visual indication means is present in the sight member.

Dispersal valve 10 which is shown in grater detail in my U.S. Pat. No. 5,076,315, includes a fluid inlet 13 on one side of housing 17 and a fluid outlet 12 located on the opposite side of housing 17. A rotary plug 14 permits a user to control the velocity of the fluid mixing stream that can be directed through the dispersal valve. A further example of a dispersal valve with a rotatable plug for controllably directing a fluid mixing stream through the dispersal valve to dispense materials such as bromine and chlorine into swimming pools, hot tubs, spas, and the like is shown in greater detail in U.S. Pat.

No. 4,662,387. A beneficial feature of such a dispersal valve is that the mixing of the dispersant chemicals is done completely within the dispersal valve so that when the fluid mixing stream returns to the liquid stream through the dispersal valve, the mixing stream can be further mixed with the liquid stream flowing through the dispersal valve thus assuring that higher concentrations of dispersant chemical are not directly introduced into the liquid stream which is returned to the pool or spa. That is, the dispersal valve ensures that the dispersant is always introduced in diluted form into the liquid stream so that the chances of human contact with high concentrations of dispersants in the pool or the spa is minimized.

Figure 1:
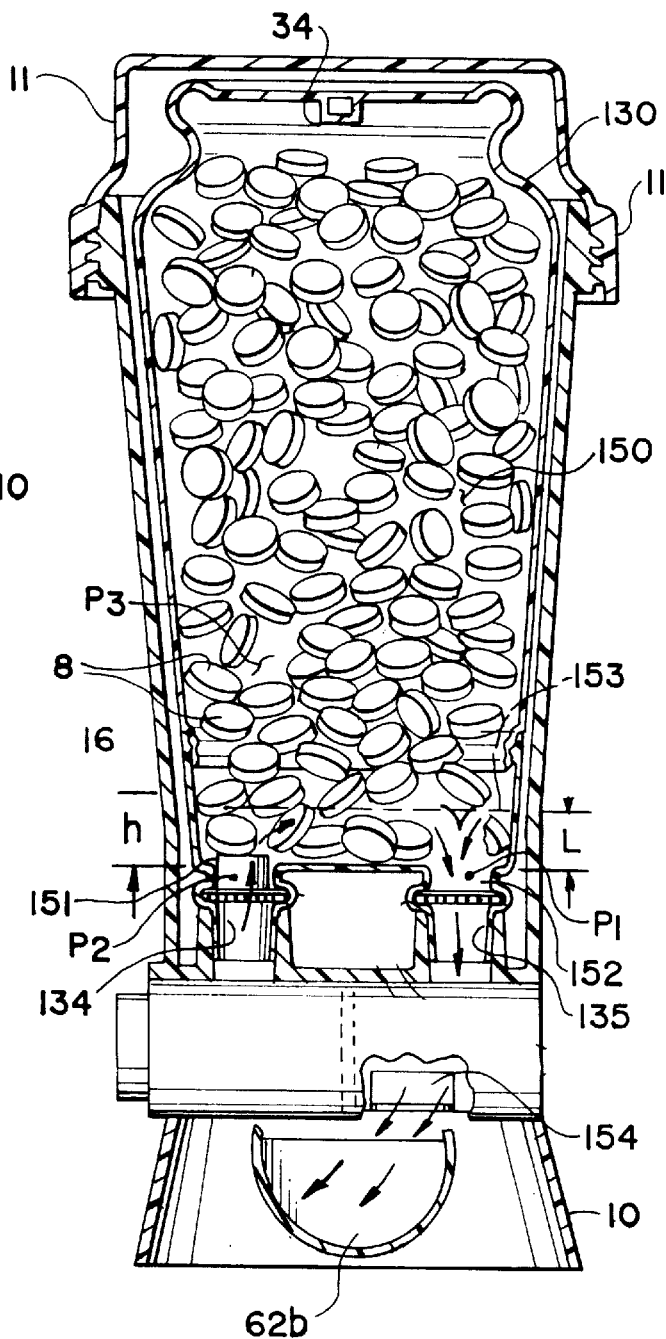
FIG. 1 is a partial cut-away view of the dispersal valve of FIG. 2 with a single canister.

FIG. 1 illustrates prior art dispersal valve 10 and a prior art canister 130 in cross-section with chlorine tablets 8 located in a trough 153. The height of trough 153 is indicated by h and the liquid level in trough 153 is indicated by L. $P_2$ indicates the pressure at the inlet passage 151, $P_1$ indicates the pressure at the outlet 152, and $P_3$ indicates the pressure in the air pocket 150. In the embodiment shown the tablets 8 in air pocket $P_3$ remain free of contact with liquid and remain in an undispensed state. However, the tablets 8 located in trough 153 are in contact with the liquid resulting in the dispensing of dissolvable or erodible tablets directly into the liquid in proportion to the rate of liquid flowing past the tablets and the amount of liquid in contact with the surface of the tablets. Consequently, the use of a dispersal valve that directs only a portion of a fluid mixing stream through the trough permits a user to controllably dispense the dispersant in the trough at a substantially constant rate over an extended period of time. In addition, the use of a canister that continually funnels unspent dispersant into the trough permits one to controllably dispense material at a substantially constant rate for two weeks or longer.

Figure 3:
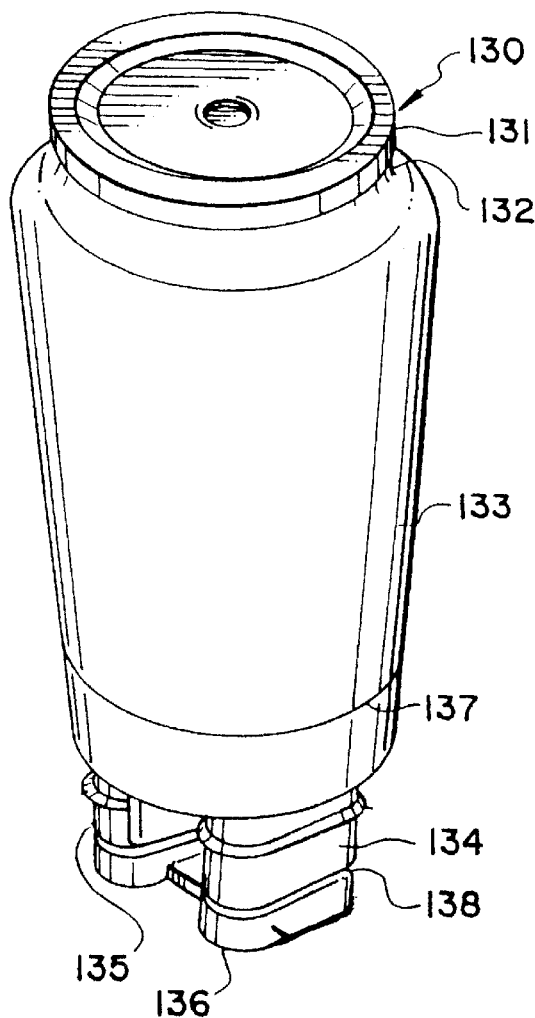
FIG. 3 is a perspective view of the canister for use in the dispersal shown in FIG. 1 and FIG. 2.

FIG. 3 shows a perspective view of a prior art canister 130 having a hand grip ridge 131 with a finger recess 132 to permit a user to lift canister 130 out of a dispersal valve. Canister 130 comprises a housing having an upper region 133 and a lower region having a first fluid port 134 and a second fluid port 135. A cap 136 extends over ports 134 and 135 to seal the canister during storage. A break line 138 extends around each of the ports to permit cap 136 to be quickly separated from canister when the canister is in use. A mating line 137 identifies where the top part and the lower part of canister have been joined together to form a closed canister.

The present invention includes canister embodiments for dispensing at least two bacteria killing materials into a pool, spa or the like. FIGS. 4 through 10 show one embodiment that uses nestable canisters to simultaneously dispense two bacterial killing materials, FIG. 11 shows a second embodiment of two side by side canisters for dispersing two bacteria killing materials and FIGS. 14 through 17 show a third embodiment of a single canister for simultaneously dispensing two bacteria killing materials.

Figure 4:
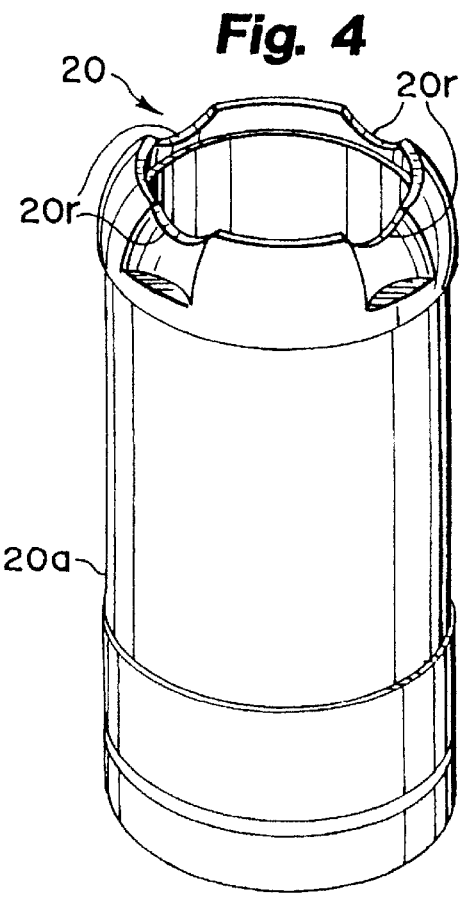
FIG. 4 is a perspective view of a first nestable canister for use in the dispersal valve of FIG. 1.

FIG. 4 shows a perspective view of an annular nestable canister 20 for use in dispersal valve 10. Nestable canister 20 nests with a second nestable canister 40 (FIG. 6) to provide one embodiment of my multiple delivery or dispensing system. Nestable canister 20 includes an outer cylindrical exterior 20a that enables canister 20 to be inserted into the existing dispersal valves in a manner that a single canister would be inserted. In addition, nestable canister 20 has a central area where a second nestable canister can be placed therein. Nestable canister 20 includes relief areas 20r to enable a person to grasp nestable canister 20 when it is within a dispersal valve. Nestable canister 20 is made from a rigid polymer plastic and normally stands in an upright position in a dispersal valve.

Figure 4A:
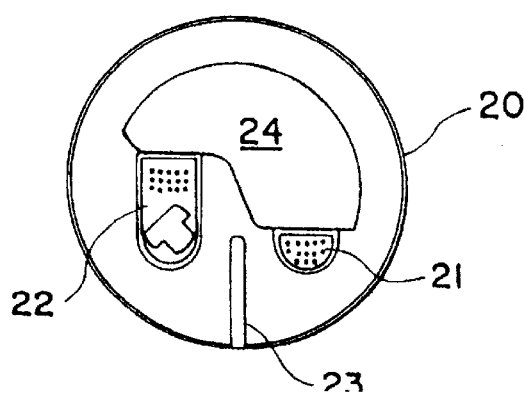
FIG. 4A is a bottom view of the nestable canister shown in FIG. 4.

FIG. 4A shows a bottom view of a nestable canister 10 having a canister inlet 21 and a canister outlet 22. A slot 23 in canister 20 provides a key for ensuing that the canister is properly inserted into the dispersal valve that has a corresponding mating tab.

Figure 4B:
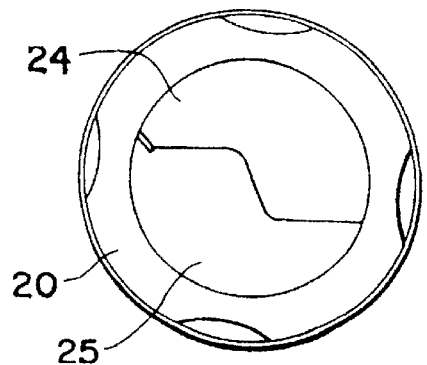
FIG. 4B is a top view of the nestable canister shown in FIG. 4.

FIG. 4B shows a top view of canister 20 revealing the lower radial inward extension 25 that holds means for directing fluid in and out of canister 20. Radial inward extension 25 extends only partway across the bottom portion of canister 20 leaving a central opening in canister 20. Reference numeral 24 identifies the central opening 24 in nestable canister 20 to enable the nesting and operation of a second canister within canister 20.

FIG. 5 shows an exploded cut-away view of nestable canister 20 and a manifold 30 that can be used to connect a set of nestable canisters to an existing dispersal valve. Nestable canister 20 includes an upper cylindrical section 26 having an annular chamber defined by a cylindrical inner wall 26b and an outer cylindrical wall 26a. Located within the annular chamber defined by walls 26b and 26a is a longitudinal rib 27 that forms both a separator and spacer between inner wall 26b and outer wall 26a. Rib 27 extends upward from cylindrical base 28. The rib 27 terminates in the top portion of section 26 in the annular chamber 31 that extends around the top portion of cylindrical section 26.

Longitudinal rib 27 divides the space between walls 26b and 26a so that water flowing from the inlet of canister 20 cannot flow directly to the outlet of the canister 20 but must pass through the water treatment minerals 35 in canister 20. The minerals for the water treatment are shown located between the inner wall 26b and outer wall 26a and are preferably a contact water treatment mineral 35 for removal of bacteria and algae from the water.

In the embodiment shown the water treatment minerals 35 can be any of a number of different minerals. Various water treatment minerals are described herein and are suitable for use in the present dual dispensing system. Water treatment mineral which are described in my earlier co-pending applications contain zinc particles and zinc particles coated with silver metal or silver chloride which are dispersed within an acid absorber such as limestone. The limestone is used to absorb acids generated within the dispenser.

The present invention includes four improved water treatment minerals which maintain the integrity of the water treatment composition by reducing the opportunity for unwanted by-products while still effectively killing bacteria. One improved water treatment mineral comprises zinc metal particles, uncoated limestone and limestone particles at least partially covered with silver chloride. A second improved water treatment mineral comprises limestone, zinc metal and at least a portion of the zinc metal covered with silver chloride and an outer protective layer of porous epoxy over the silver chloride. A third improved water treatment mineral comprises limestone, limestone partially coated with silver chloride and zinc carbonate. A fourth water treatment mineral comprises uncoated limestone particles and limestone particles at least partially covered with silver chloride.

The water treatment composition using zinc particles and silver for killing bacteria and inhibiting algae growth in a recirculating water system comprises a plurality of zinc particles having a maximum dimension on the order of 1/8 of an inch, with the zinc particle having an exterior irregular surface coated with silver. The silver is sufficiently thick so as to kill bacteria that comes into contact with the silver. In most applications, the water treatment composition has a coating of silver which is about 1% of the weight of the silver coated zinc particle. In general, the water treatment composition of mineral dispersants used in canister 20 includes zinc particles having sufficiently small dimensions so that sufficient contact can be made with the silver on the zinc to provide effective killing of bacteria and algae. In addition to the silver coated zinc particles, the composition includes uncoated zinc particles dispersed throughout the mixture of the dispersant composition in nestable canister 20. The use of a contact type bactericide in the second canister in conjunction with the water treatment minerals makes it possible to lower the levels of chlorine used in the pools. That is, chlorine levels in the pool or spa do not need to maintained at high levels as a portion of the bacteria killing can be done outside the pool or spa by the contact bactericide in the second canister.

The canister 20 includes an acid absorber (limestone) with the acid absorber available for absorbing acids which are generated by the production of chlorine in another dispensing canister 40 (FIG. 6) located in the fluid system. Thus, a dependent relationship exists between the two canisters with the canister 20 carrying materials that absorb undesirable by products from the chemical dispersant in another canister.

To illustrate the internal operation of nestable canister 20, reference should be made to FIG. 5 which shows base 28 and base plate 29 that sealably fasten to each other with the base 28 further sealably fastened to member 26. FIG. 5 shows that extension 25 extends only across the bottom portion of nestable container 20. Extension 25 has an internal passage (not shown) that directs fluid from inlet 21 vertically upward into half of an annular chamber defined on the ends by end longitudinal rib 27a and end longitudinal rib 27b and on the sides by the outer cylindrical member 28a and inner cylindrical member 28b. The three arrows extending upward from base 28 indicate the direction of incoming flow in nestable canister 20. That is, fluid enters inlet 21 and is directed by the passages in extension 25 into the half annular inlet chamber where the fluid travels upward though the dispersant as indicted by the arrows. Once the fluid reaches the top of canister 20 it flows over the end of longitudinal rib 27 and downward to the outlet in canister 20. In order for the fluid to be discharged from the nestable container the fluid must flow downward through additional mineral dispersant wherein it is discharged from the canister after it passes into extension 25 which through an internal passage (not shown) directs the fluid to outlet 22.

In fluid operation of nestable canister 20, a portion of the fluid mixing stream from a dispersal valve 10 is directed through inlet 21 wherein it flows upward through the dispersant located in one side of nestable canister until the fluid reaches the top of canister 20. Once the fluid passes around rib 27 the fluid flows downward through a similar chamber containing additional dispersant until the fluid is discharged through outlet 22.

Located below nestable canister 20 is a manifold 30 for use in adapting the nestable canister for use in existing dispersal valves. In certain applications manifold 30 is not needed; however, in some applications the manifold can be used to allow a wide variety of nestable canisters to be used in various types of dispersal valves.

FIG. 5A shows a bottom view of manifold 30 and FIG. 5B shows a side view of manifold 30 while FIG. 5 reveals the interior of manifold 30. Manifold 30 includes a first extension 30a for engaging an outlet port of a dispersal valve and a second extension 30b for engaging an inlet port of a dispersal valve. FIG. 5a shows that the bottom of manifold 30 includes an enlarged outlet 30c for engaging with inlets from two or more nestable canisters and an enlarged inlet 30d for engaging with outlets from two or more nestable canisters.

FIGS. 6 and 7 show a second nestable canister 40 therein. FIG. 6 shows a side view of nestable canister 40 and FIG. 7 shows a partial cutaway view of nestable canister 40. Nestable canister 40 comprises a cylindrical outer wall 40a with reinforcing groves 40b to provide stiffness to internally nestable canister 40. A first finger grip 41 enables the nestable canister 40 to be lifted from or lowered into the nestable canister 20. Nestable canister is preferably made from a polymer plastic or the like.

Nestable canister 40 includes an inlet port 43 for engaging a portion of the inlet flow from a dispersal valve and a fluid outlet port 44 for directing the portion of the fluid back into the main liquid stream. The cutaway view shows dispersant tablets 9 located within nestable canister 40. Tablets 9 can typically be chlorine tablets for killing bacteria. The operation of nestable canister 40 is similar to the operation of nestable canister 130 shown in FIG. 2 except that nestable canister 40 does not received all the fluid mixing stream from valve inlet member 134. That is, the fluid mixing stream that flows through the dispersal valve is bifurcated so that a first portion of the incoming fluid mixing stream is diverted through the dispersant in nestable canister 40 and a second portion of the fluid mixing stream is directed through the nestable canister 20.

FIG. 8 is a view that illustrates that nestable canister 40 can be axially inserted within the nestable canister 20. Nestable canister 40 includes an outer dimension designated by $W_1$ and nestable canister 20 includes an inside dimension designated by $W_2$ with $W_2$ greater than $W_1$ so that canister 40 can be freely inserted within the chamber formed by the interior of canister 20. FIG. 8 shows the two nestable canisters 40 and 20 prior to their insertion into a nesting relationship with each other.

Figure 9:
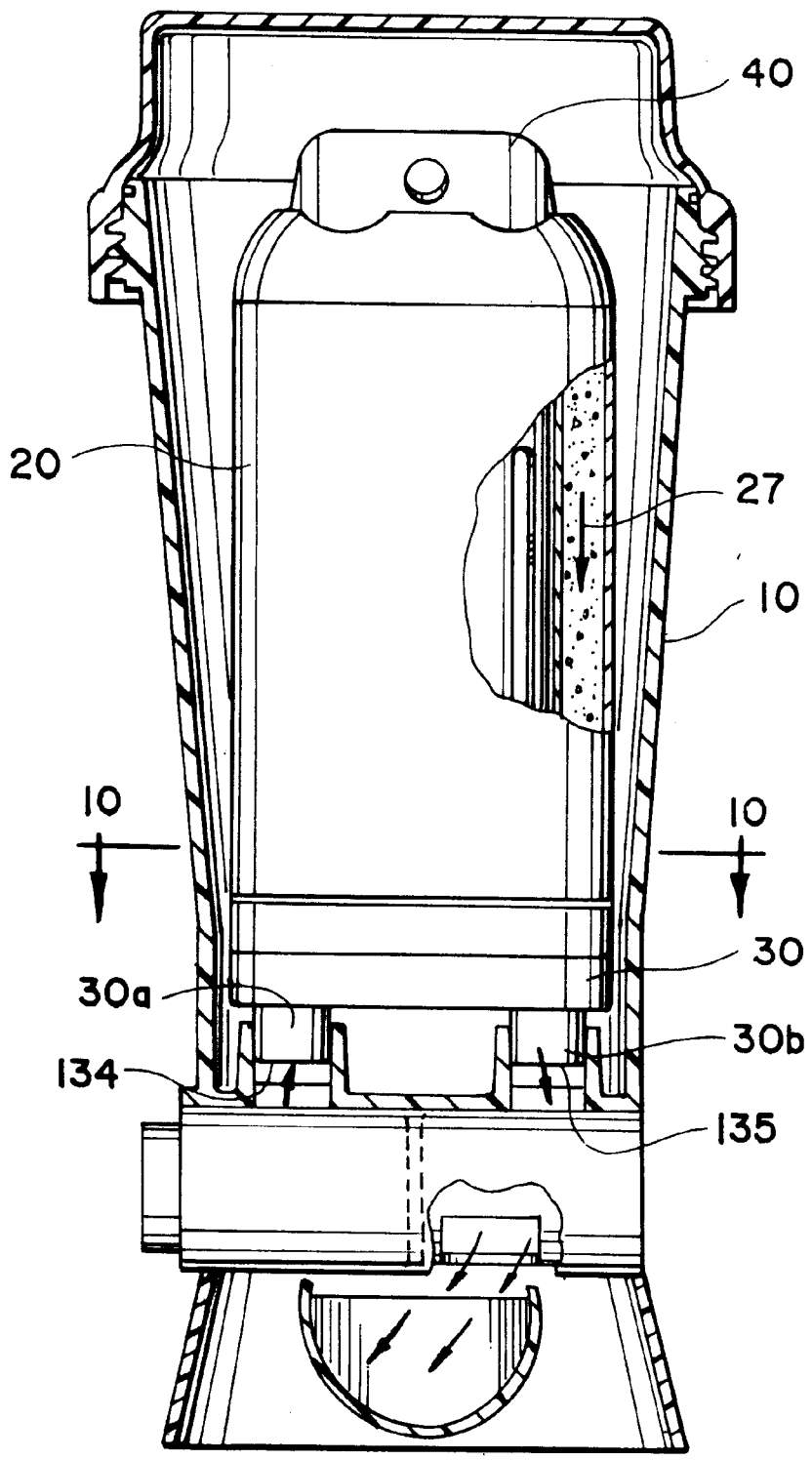
FIG. 9 shows a partial cutaway view of a side elevation of a dispersal valve containing nestable canisters therein.

FIG. 9 shows a partial back cutaway view of dispersal valve 10 with nestable canister 20 and nestable canister 40 located in nesting relationship within the space formally occupied by canister 130. Manifold 30 directs a fluid mixing stream from valve inlet 134 into valve inlet 30a and manifold outlet 30b directs the fluid mixing stream together with the two dispersant back into the main liquid stream.

Figure 10:
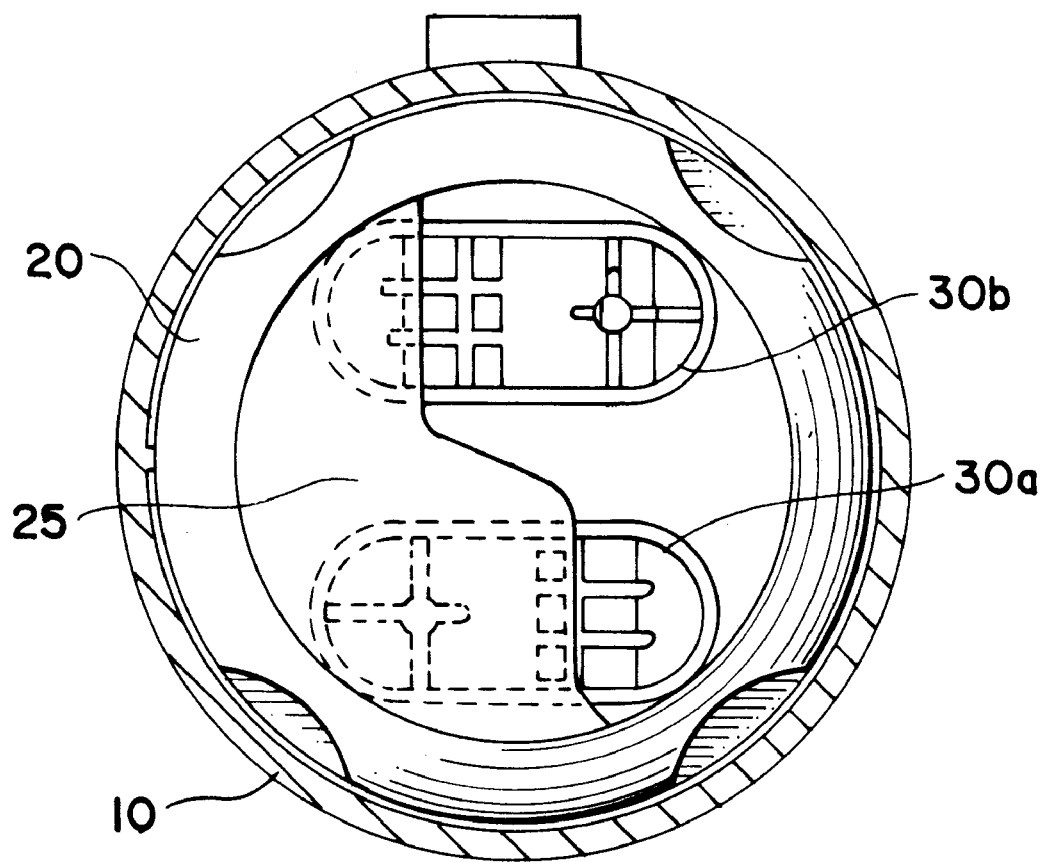
FIG. 10 shows a cross-sectional view taken along lines 10—10 of FIG. 9 with the inner nestable canister removed for clarity.
Figure 11:
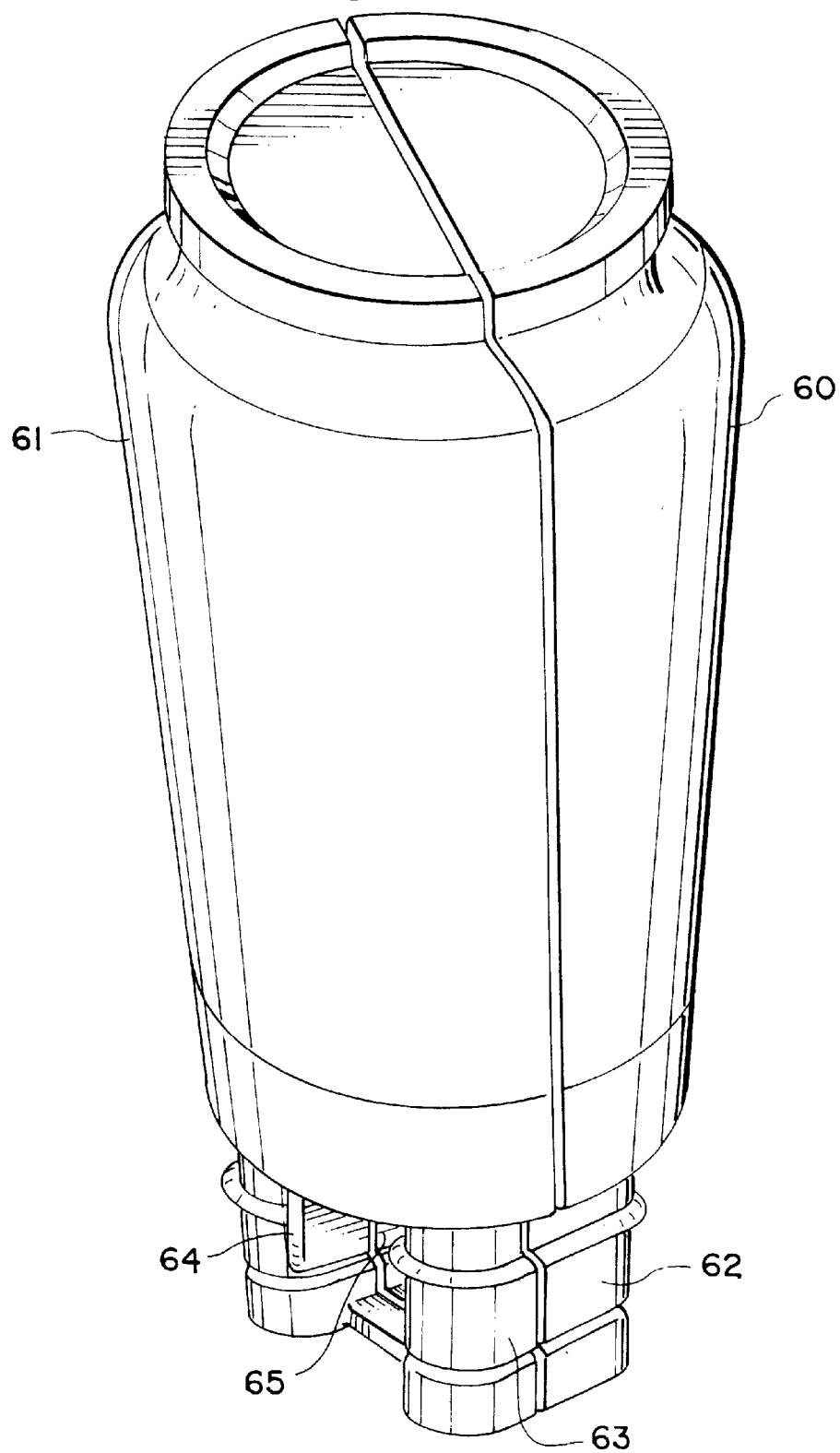
FIG. 11 is a perspective view of an alternate embodiment of dual canisters for insertion into a dispersal valve.

FIG. 10 shows a cross-sectional view of canister 10 with the inner nestable canister 40 removed to show that nestable canister 20 extends over a portion of first manifold port 30a and second manifold port 30b. Thus there is a fluid path that provides for receiving a portion of the fluid mixing stream and allowing the portion of the fluid mixing stream to flow through the outer nestable canister 20. The remaining portion of the mixing fluid stream which is directed through the other portions of fluid ports 30a and 30b is directed through the second nestable canister which has inlets and outlets positioned to receive and dispense the other portion of the mixing fluid stream back into the dispersal valve. Thus, the fluid mixing stream is bifurcated allowing portions of the bifurcated fluid mixing stream to be simultaneously but separately mixed with different chemical dispersants. After mixing of the chemical dispersant with the bifurcated fluid stream, the two portions of the stream are combined in the dispersal valve before being directed back into the main liquid stream flowing through the dispersal valve.

The water treatment system shown in FIGS. 4–10 enables a person to dispense a single chemical dispersant or multiple chemical dispersants into the pool or spa by merely selecting the appropriate canisters for use in the dispersal valve to thereby provide a water treatment system for killing bacteria and algae in a recirculating water system. That is, with one canister including a first bacteria killing chemical (such as a solid chlorine tablet or stick) one can dispense chlorine into the recirculating water system to kill the bacteria in the water system and with another canister, which includes a mineral having in situ bacteria killing capabilities one can maintain the level of chlorine at a lower level. That is, one can kill bacteria on contact by having bacteria killing minerals in the other canister. In the embodiment shown, the water treatment system is installed in a single compartment dispersal valve with the first canister and the second canister located in nesting relationship in the compartment of the dispersal valve. Not only can both bacteria killing chemicals and bacteria and/or algae killing minerals be dispensed into the system, one can vary the dispensing rate by using a valve on the dispersal valve for varying the amount of water flowing through the dispersal valve. A further benefit of the invention is that the use of multiple nestable containers can be used to lower the amount of water circulated through the dispersant in the valve. For example, a normal setting of the dispersal valve with a single canister might deliver chemical dispersants at a rate of x per hour. With the present invention one of the multiple canisters might deliver chemical dispersants at a rate of 0.7x per hour. Thus the present invention allows the user to lower the dispersal rate by inserting a second canister to receive a portion of the mixing fluid stream in the dispersal valve. For example, the table below lists the output of a dispersal valve with a single canister containing chlorine tablets to a dispersal valve containing a set of nestable canisters, one containing chlorine tablets and the other containing zinc particles, silver coated zinc particles and limestone.

| Dial Setting | Chlorine (oz/chlorine per hour) | Chlorine & Minerals (oz/chlorine per hour) |
| --- | --- | --- |
| 0 | .016 | .014 |
| 3 | .135 | .080 |
| 4.5 | .149 | .142 |
| 6 | .677 | .313 |
| 9 | 1.630 | .372 |

Thus nestable containers can be used to change the calibration of the valve to allow the dispersal valve to be used with differently sized bodies of water.

In the above example, the minerals in the second canister are comprised of zinc (35.7 grams), silver coated zinc (237 grams), and limestone (907.2 grams). The zinc acts as a carrier for the silver which is applied to the zinc in form of a silver halide emulsion. The emulsion is applied in the form of paste and fixed through the use of a combination of heat, halogen light and a chemical developer. This fixing process converts the silver halide emulsion to silver which securely adheres to the zinc during the fixing process. The end result is a particle that has a complete coating of silver (about 1% silver to the weight of the zinc). The limestone has a nominal size of about ¼ of an inch. Thus, the combination of a chlorine and silver and zinc dispersant composition is effective in killing bacteria and killing algae with the chlorine providing the fast killing action and the silver and zinc providing the long term killing action.

FIG. 11 shows an alternate embodiment wherein the nestable canister are formed into two longitudinally extending hemicylindrical canisters 60 and 61. Canisters 60 and 61 are separate canisters for holding the contents of each in isolation from each other. In the canisters 60 and 61, the fluid from the dispersal valve is split and is sent upward through the inlet ports 62 and 63 and through the respective canisters where it is discharged through the outlet ports 65 and 64.

A process to form a water treatment composition in pellet form suitable for insertion into an inline feeder in a water supply is as follows. The water treatment comprises zinc pellets with a coating of silver chloride (AgCl) located thereon. To obtain the coating, the silver chloride particles are suspended in an adhesive matrix that adhesively secures the silver chloride particles proximate to the surface of the zinc pellets to produce a zinc pellet with a silver chloride coating. The matrix allows both the silver and the zinc to remain in a reactive state so that both the silver and zinc can be used in water treatment systems.

Silver chloride is a white powder that can be melted or cast like a metal, and is derived from heating a silver nitrate solution and adding hydrochloric acid or salt solution to produce a silver chloride solution which is then boiled or filtered in the dark or under a ruby red light to produce the silver chloride powder. The silver chloride, while still in solution, is combined with an adhesive to form an adhesive silver chloride solution. The adhesive and the silver chloride solution are then applied to the zinc pellets. The adhesive is then cured to produce zinc pellets having a silver chloride coating adhesively adhered thereto with both the zinc and the silver chloride available for reacting with the chemicals within a bacteria cell to kill or damage the bacteria. The term adhesively secured herein is meant to include a surface attachment structure between two bacterial adhering materials that does not prevent either of the bacteria adhering materials from binding with the bacteria in the water to damage or destroy the bacteria in the water. While the process has been described with adherence of the silver chloride to zinc particles, the process also works for securing of silver chloride to other particles such as the limestone particles used in the water treatment composition.

Figure 12:
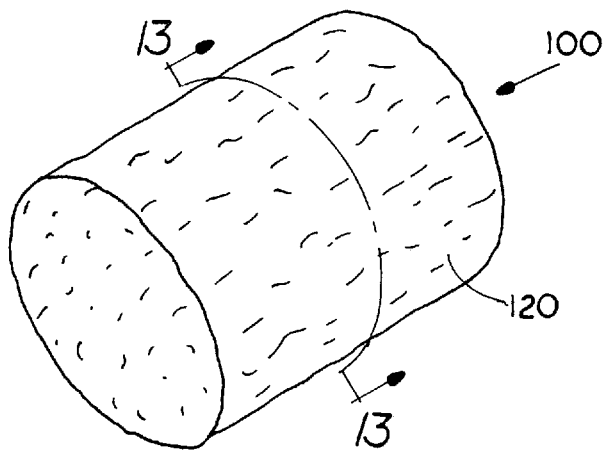
FIG. 12 is a perspective view of zinc pellet having a matrix carrying a silver yielding ion thereon.
Figure 13:
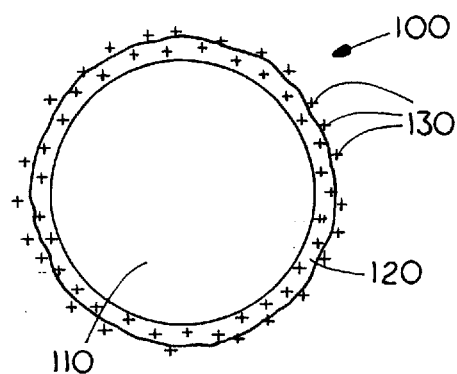
FIG. 13 is a sectional view taken along lines 2—2 of FIG. 1 to show the adhesive matrix located around the zinc pellet.

Referring to FIGS. 12 and 13, a water treatment pellet 100 is shown, which in this embodiment is a zinc pellet having an adhesive matrix coating 120. Adhesive matrix coating 120 comprises an adhesive that secures itself to the surface of both the silver chloride 130 and to the zinc pellet 110 without preventing either the zinc or the silver chloride from adhering to and damaging or killing bacteria located in the water. The process is described in relation to forming a silver coating on a zinc pellet so that both the zinc and the silver remain in a reactive state to react with the chemicals in the bacteria and effectively damage or kill the bacteria. While the preferred carrier for the silver chloride comprises zinc pellets, the carrier need not be zinc as long as the carrier is compatible with the bacteria adhering material on the carrier. The silver chloride coated particle 100 is shown to be in the form of a cylinder and is cut from zinc wire, however, any of many different shape pellets could be used with the present invention.

FIG. 13 is a cross-sectional view of the silver chloride coated pellet 100 of FIG. 1 showing zinc particle 110 centrally located within adhesive matrix 120 that contains silver chloride 130 dispersed throughout the adhesive matrix 120. As can be seen from the drawing, the silver chloride 130 is maintained in the matrix proximate the zinc pellet 110 to enable water to contact both the zinc and the silver chloride located within the matrix.

In one water treatment composition usable in the canister and described in my earlier co-pending applications, one coats a particle such as a zinc pellet with a silver ion yielding material such as silver chloride by adhesively affixing or securing the silver chloride and the zinc pellets proximate to each other through a non-soluble water porous adhesive matrix. In one of the improved water treatment compositions of the present invention, one coats limestone particles with a silver ion yielding material such as silver chloride by adhesively affixing or securing the silver chloride and the limestone particle proximate to each other through a non-soluble water porous adhesive matrix in the manner and method used to secure the silver chloride to the zinc metal particles.

A suitable material for adhesively securing the silver chloride proximate the particles is commercially available gelatin which can be cross linked with an aqueous solution of formaldehyde or glutaraldehyde to form a non-soluble water penetrable matrix on the exterior surface of the carrier.

One process of making a water treatment composition includes the use of a plurality of carriers or water treatment members, typically an 1/8 inch or smaller, which are suitable for inserting into an inline feeder. The carrier can be formed from zinc wire by cutting the zinc wire into cylindrical sections about an 1/8 of an inch long or if desired the carrier can be formed from limestone particles.

The following two examples illustrates how a silver chloride coating was affixed proximate to the exterior surface of a zinc pellet.

EXAMPLE 1

In order to coat a batch of zinc pellets with an adhesive matrix containing silver chloride, 12.5 grams of silver nitrate was mixed in 25 ml of distilled water to form an aqueous silver nitrate mixture.

1.5 grams of gelatin was then mixed in 25 ml of distilled water to form a gelatin mixture. The gelatin mixture was heated to a temperature of about 140 degrees F.

To eliminate lumps in the gelatin mixture, the gelatin mixture was strained through a screen. At this point 5 grams of sodium chloride were mixed into the gelatin mixture. The gelatin mixture was then combined with the aqueous silver nitrate mixture to convert the silver nitrate into silver chloride to thereby form an aqueous silver chloride gelatin mixture. A batch of zinc pellets having a maximum dimension of about 1/8 inch were heated to about 140 degrees F. The pellets were then sprayed with the heated aqueous, silver chloride, gelatin mixture. In order to form a matrix to affix the silver chloride to the zinc pellets, the silver chloride gelatin mixture was immersed in an aqueous bath of glutaraldehyde for about 12 hours to react the gelatin with the glutaraldehyde. The curing produced an adhesive matrix that secured the zinc pellets with the silver chloride dispersed throughout the adhesive matrix. After curing, the zinc pellets, which are covered with a coating of silver chloride, were rinsed and air dried to produce zinc pellets with a silver chloride coating affixed proximate to the zinc pellets.

EXAMPLE 2

The above process was repeated except instead of immersing the zinc particles with the silver chloride gelatin mixture in an aqueous bath of formaldehyde, the zinc particles with the silver chloride gelatin mixture were cured in an aqueous bath of formaldehyde.

In the above examples the zinc pellets had a maximum dimension of about 1/8 of an inch. Larger or smaller pellets could be used; however, for use as a water treatment composition in a dispensing valve it is preferred to have carrier in multiple pellets in order to present a large surface area to the water containing the bacteria.

In the preferred method, the adhesive used was gelatin as the gelatin is capable of adhering to the surfaces of both the zinc and the silver chloride. That is, gelatin, which can be cross-linked in the presence of formaldehyde or glutaraldehyde to obtain the necessary adhesive characteristics, remains non-soluble in the water and unreactive with either the zinc or the silver chloride and thus can hold the silver chloride proximate the zinc. That is, the cross-linked gelatin not only forms a surface attachment but forms a matrix to support or secure the silver chloride in proximity to the surface of the zinc pellet. As the gelatin matrix is securable to the surfaces of both the silver chloride and to the zinc pellets, one is assured that the silver and zinc will remain proximate each other so that the regenerative, coactive relationship between the zinc and silver can be retained. While other adhesives could be used, gelatin is preferred as it does not leave unwanted residues that might be dissolved in the water during the water treatment process. Also the gelatin is desirable since the porosity of the adhesive matrix formed from gelatin allows bacteria containing water access to both the zinc and the silver to enable both the zinc and the silver to coactively kill the bacteria in the water.

In an improved water treatment composition, the zinc pellet with the silver chloride coating is covered with a layer of epoxy. The epoxy has sufficient porosity to permit the migration of silver ions therefrom and ensures that the silver chloride remains in an unreactive state on the zinc pellet. The combination reduced the generation of unwanted by-products during use of the water treatment composition.

Figure 14:
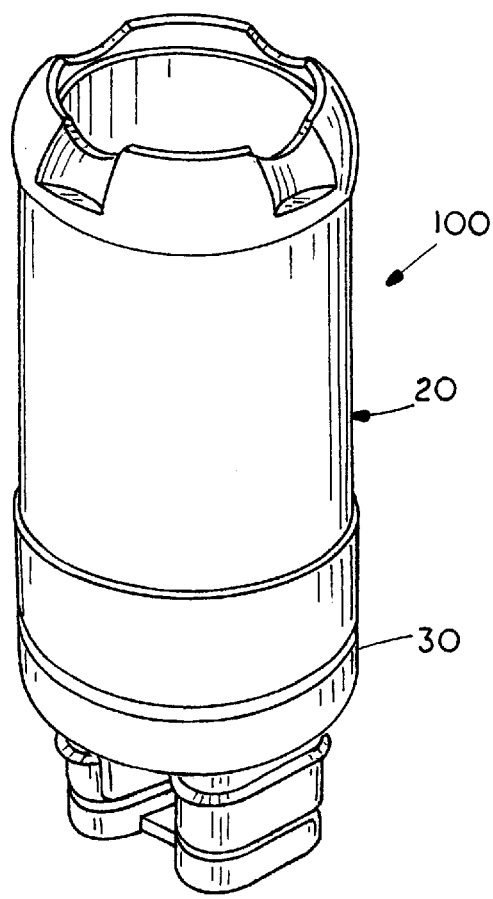
FIG. 14 is a perspective view of my single canister for simultaneously dispersing two dispersants.

Referring to FIG. 14 reference numeral 200 identifies the annular canister 20 and reference numeral 30 identifies the manifold that is secured to the bottom to form an annular dispenser which is shown in exploded view in FIG. 5.

FIG. 15 shows the use of canister 200 in a slightly different manner than in the canisters shown in FIGS. 4–10. Instead of placing a second canister 40 within annular canister 20, free-sitting chlorine tablets 201 are placed directly in the cylindrical compartment, chamber or recess 202 formed by the upright cylindrical walls of canister 20. In the embodiment shown in FIG. 15, a portion of the water flows through the annular canister 20 and a further portion that would normally flow through a nestable canister located in chamber 202 flows around a solid support surface 206a, which in the embodiment shown, includes a divider platform 206 and then through the chamber 202 where the free sitting chlorine tablets 201 are located. The arrows indicate that the water generally flows upward along one side of the annular canister 20 and returns by flowing downward along the opposite side of the canister 20. In the embodiment of FIG. 15 it is apparent that a single canister can be used to disperse both the bacteria killing minerals and the bacteria killing chemicals as the solid tablets are confined within the side walls of the canister 20. Thus, the cost of the water treatment system of FIG. 15 is reduced as one need only replenish the chorine tablets and not a separate canister and the chlorine tablets. However, for those who want to avoid the handling of chemicals, the nestable canister 40 shown in FIG. 8 can be inserted therein to contain the solid bacteria killing chemical which can for example be chlorine or bromine tablets.

FIG. 16 shows a top view of the inside of canister 20 showing divider platform 206 for supporting free-sitting solid tablets. In the condition shown in FIG. 15, the divider platform can maintain the free sitting tablets free of the ports 30e and 30f. As can be seen in FIG. 16, the manifold 30 partly covers the passages 30a and 30b to direct a portion of the fluid through the annular canister while a further portion flows through the central chamber in canister 30. That is, passage 30*b* has two portions, a first portion 30*d* which extends partially under the inlet to the annular canister 30 and a second portion 30*e* that directs fluid upward into the compartment centrally located within the sidewalls of the annular canister 30. Similarly, passage 30*a* has two portions, a first portion 30*c* which extends partially under the outlet to the annular canister 30, and a second portion 30*f* that directs fluid downward into the dispersal valve. The inlet port 30*b* functions to direct a portion of the fluid into the inlet of the annular canister 30 and a further portion into the central chamber 202. Similarly, the fluid returns from the recess in annular canister 30 through a passage identified as 30*f* and the fluid flowing through annular canister 30 returns through passage 30*c*. In order to accommodate the variously sized solids in chamber 202 and to ensure that the fluid circulates through the chamber 202, a divider platform 206 is included to isolate the two ports from direct contact with the solid tablets which, if of the incorrect size, could interfere with the flow through the chamber 202. The divider platform 206, as shown in FIG. 15, functions as a solid support surface 206*a* for holding a free sitting solid bacteria killing chemical 201 away from outlet port 30*b* to prevent blockage of outlet port for dispersing the bacteria killing chemical back into the water treatment system. A first web 206*b* extends upwardly to support surface 206*a* to isolate the fluid flowing upwardly and second web 206*c* extends upwardly to support surface 206*a* to isolate the fluid flowing downwardly into port 30*b*. It should be understood that the divider platform is not necessary used in conjunction with all types of solid chemicals used in the compartment 202; however, in certain cases one wants to ensure that the solid chemicals are not so large so as to block the return flow to the dispersal valve. Thus, with use of a divider platform one is ensured that both the bacteria killing mineral and the solid bacteria killing chemical can be simultaneously dispensed into the water treatment system to kill unwanted bacteria in the water.

Figure 17:
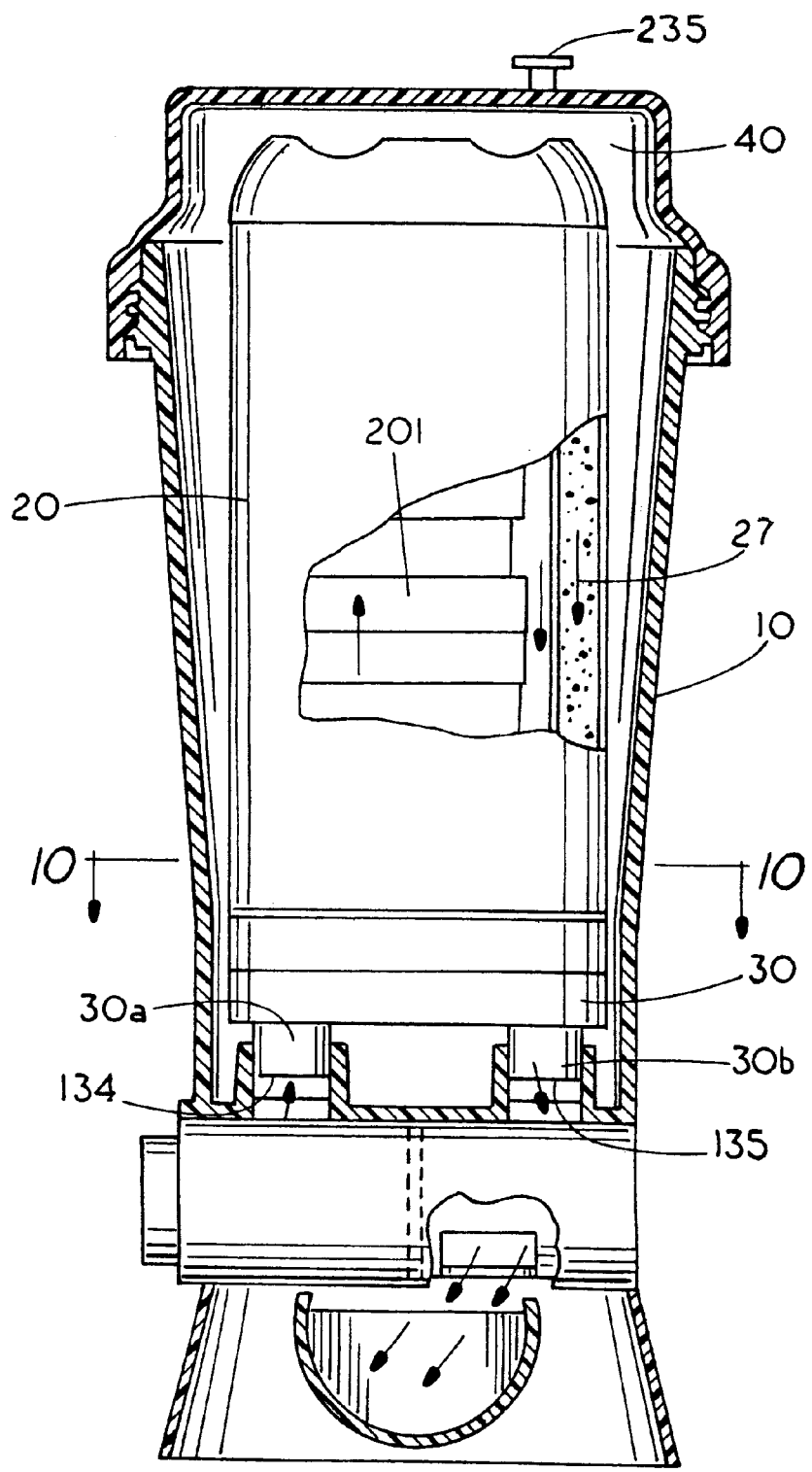
FIG. 17 is partial cutaway view showing the single canister located in a dispersal valve with the tablets having a substantially smaller diameter than the inside of the canister.

FIG. 17 shows the annular canister 20 partially in section with the free sitting-tablets 201 located therein. Thus the function of the embodiment shown in FIG. 17 and that shown in FIG. 9 are identical except that in the embodiment of FIG. 17 the solid tablets are not contained within a separate dispenser but are held in annular recess located within the side walls of the annular canister 20.

The present invention includes a mineral dispenser having upwardly extending sides for forming a first compartment and a second compartment therebetween with the first compartment having a first bacteria killing mineral therein. The mineral dispenser has an inlet for directing a portion of the water flowing through a dispersal valve into the mineral dispenser, through the bacteria killing mineral, and through an outlet for returning the portion of the water flowing therethrough to the dispersal valve. The second compartment of the mineral dispenser includes a divider platform having a solid support surface for holding a free sitting solid bacteria killing chemical away from the outlet port to prevent blockage of the outlet port for dispersing the bacteria killing chemical into the water treatment system so that the bacteria killing mineral and the solid bacteria killing chemical are simultaneously dispensed to kill the bacteria in the water.

Thus, the bacteria killing minerals can be selected from the improved group of bacteria killing minerals consisting of zinc metal particles, uncoated limestone and limestone particles at least partially covered with silver chloride; limestone, zinc metal and at least a portion of the zinc metal covered with silver chloride and an outer protective layer of porous epoxy over the silver chloride; limestone, limestone partially coated with silver chloride and zinc carbonate or uncoated limestone particles and limestone particles at least partially covered with silver chloride. While zinc carbonate is described as the preferred zinc containing material, the zinc containing material can be selected from the group of zinc containing materials consisting of zinc carbonate, zinc silicate, zinc sulfate, zinc chloride, zinc oxide, zinc hydroxide, zinc stearate or combinations thereof.

Figure 18:
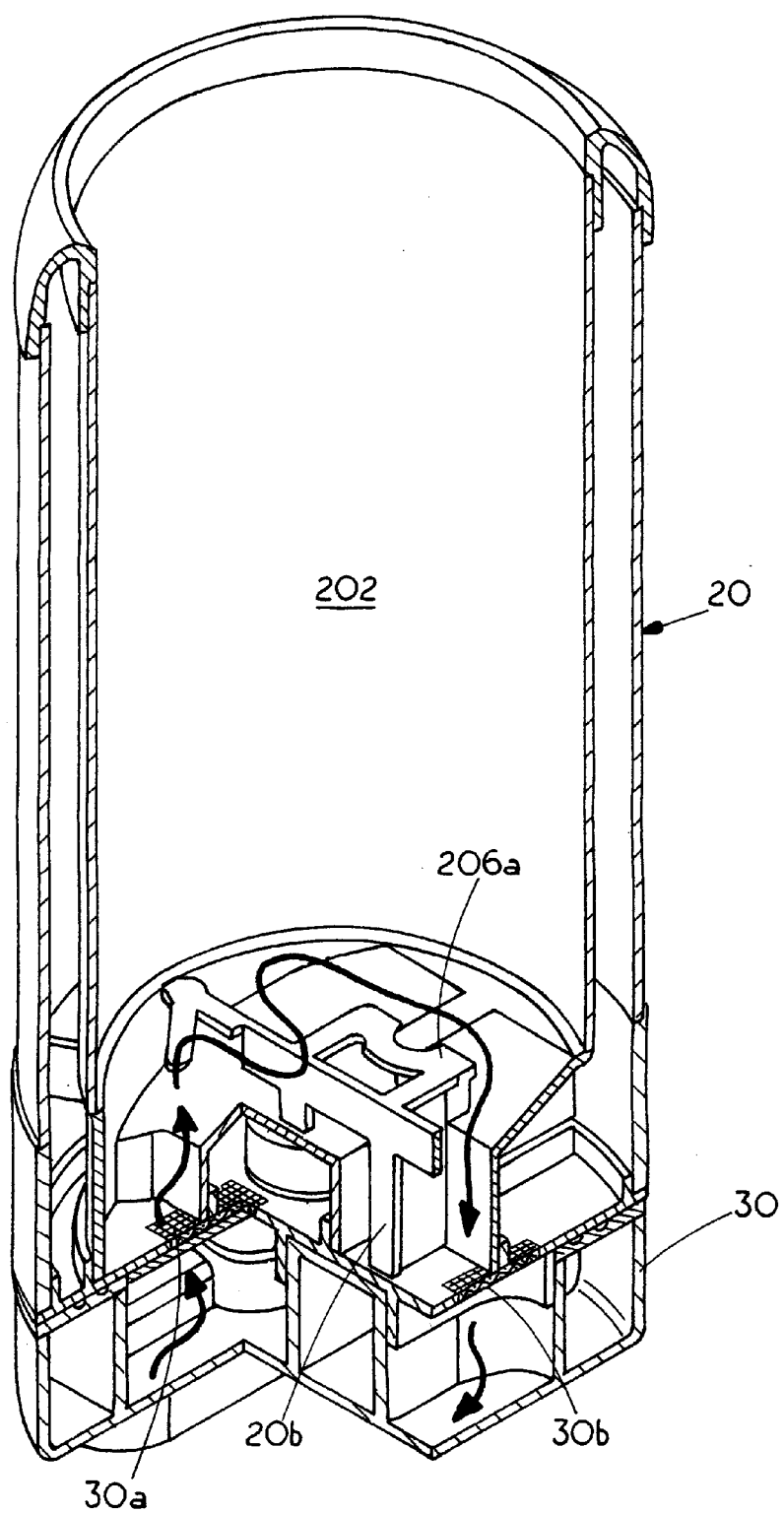
FIG. 18 is partial cutaway view showing the single canister and a flow pattern wherein the tablets in the compartment have a diameter only slightly less than the diameter of the cylindrical compartment in the single canister.

FIG. 18 is partial cutaway view showing the single canister 20 and a first flow pattern, which is indicated by arrows, when the tablets in the compartment have a diameter only slightly less than the diameter of the cylindrical compartment in the single canister. In this embodiment, the water generally flows along the bottom of the compartment 202 and erodes the lower tablet in the chamber as the water flows from inlet 30*a* to outlet 30*b*.

Figure 19:
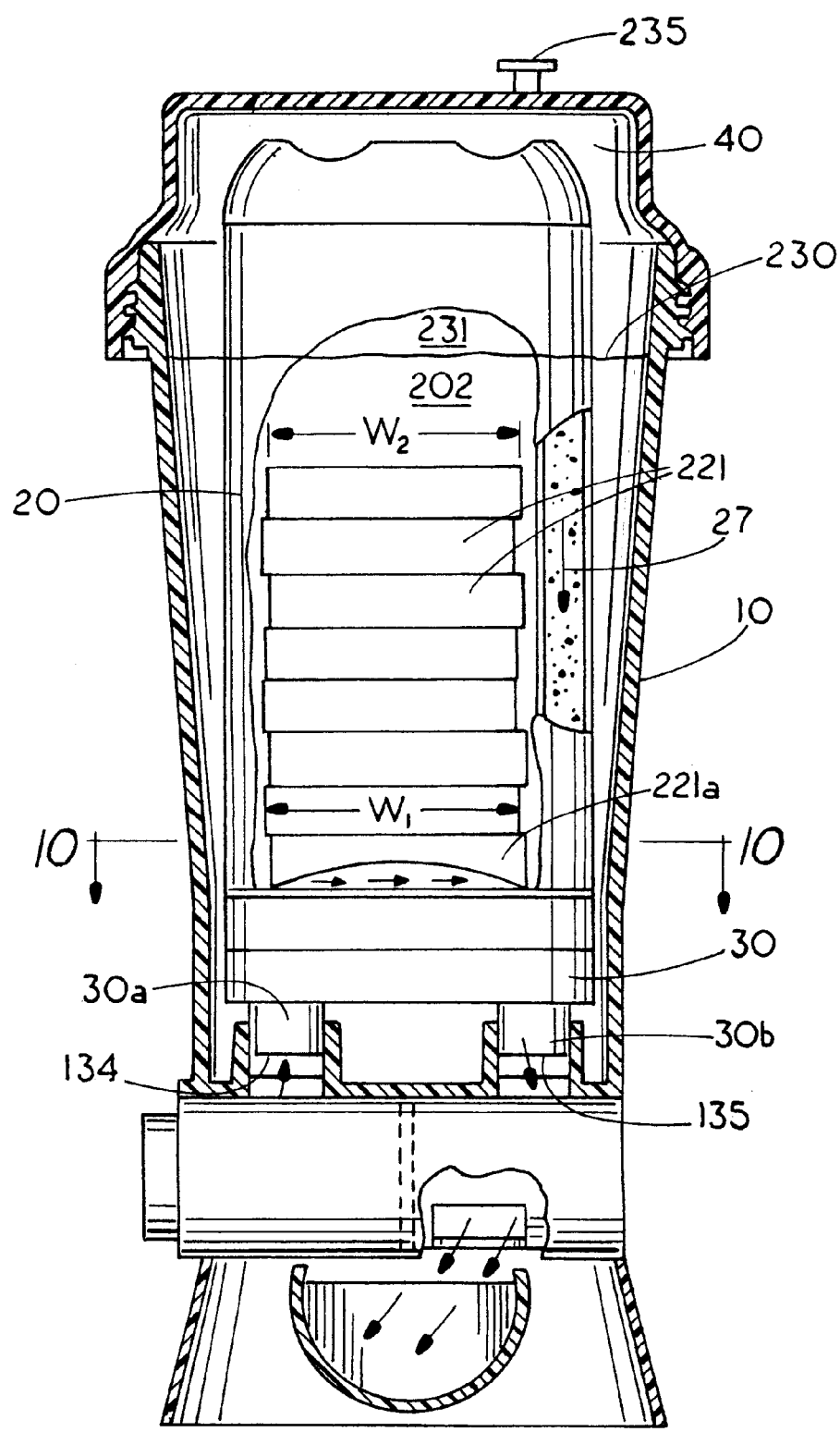
FIG. 19 is partial cutaway view showing the single canister located in a dispersal valve with the tablets having a diameter only slightly less than the diameter of the single canister.

FIG. 19 is partial cutaway view showing the single canister 20 located in a dispersal valve 10 with the tablets 221 having a diameter $w_1$ which is only slightly less than the diameter $w_2$ of the single canister. In the embodiment shown in FIG. 19, the air valve 235 has been opened to allow air into the top of the dispersal valve 10. As a result, the water level rises and is indicated by reference numeral 230 and an air pocket 231 is formed at the top of the dispersal valve. With the water level at the height indicted by reference numeral 230, the water completely covers the stack of chlorine tablets 221 in the compartment. Consequently, the chlorine can dissolve in the water. As some of the water will circulate upwardly in the compartment 202, one can increase the amount of chlorine being dispensed from the inner canister. That is, the raising or lowering of the water level 230 will determine the amount of chlorine that can be dissolved in the water with more chlorine dissolved in the water if the water level is high and less water dissolved if the water level is low.

To illustrate the erosion process, the bottom tablet 221*a* is shown with a lower portion eroded away by water flow as indicated by arrows going from left to right. Although the actual shape of erosion will vary, the drawing shown in FIG. 19 is for illustration purposes to show that the presence of a bottom tablet that is only slightly smaller than the size of the compartment urges the water to flow along the bottom and erodes away the bottom tablet more quickly as it is located directly in the path where the water normally flows the hardest and the fastest.

What is claimed is:

1. A water treatment system for killing bacteria in situ and in a main body of water comprising:

a dispersal valve for directing water therethrough;

a mineral dispenser, said mineral dispenser having upwardly extending sides for forming a first compartment and a second compartment therebetween, said mineral dispenser first compartment having a first bacteria killing mineral therein, said mineral dispenser having an inlet for directing a portion of the water flowing through said dispersal valve into said mineral dispenser, through said bacteria killing mineral, and through an outlet for returning the portion of the water flowing therethrough to said dispersal valve, said mineral dispenser second compartment including a solid support surface for holding a free sitting solid bacteria killing chemical away from said outlet port to prevent blockage of said outlet port for dispersing the bacteria killing chemical into the water treatment system whereby the bacteria killing mineral and the solid bacteria killing chemical are simultaneously dispensed to kill the bacteria in the water.

2. The water treatment system of claim 1 wherein the solid support surface is part of a divider platform located in said mineral dispenser.

3. The water treatment system of claim 1 wherein the mineral dispenser upwardly extending sides form an annular chamber for holding said first bacteria killing mineral.

4. The water treatment system of claim 1 wherein the mineral dispenser includes limestone particles with at least some of the limestone particles having a partial coating of silver thereon.

5. The water treatment system of claim 2 wherein the mineral dispenser includes limestone particles with at least some of the limestone particles having a partial coating of silver chloride thereon.

6. The water treatment system of claim 3 wherein the mineral dispenser includes a plurality of zinc metal particles.

7. The water treatment system of claim 4 wherein the mineral dispenser includes zinc metal.

8. The water treatment system of claim 1 wherein the bacteria killing mineral includes a plurality of zinc particles, said zinc particles having at least a partial coating of silver for killing bacteria coming into contact with the silver.

9. The water treatment system of claim 1 wherein the dispersal valve holds said mineral dispenser with said dispersal valve including a port for directing a portion of fluid into said mineral dispenser first compartment and a further portion into said second compartment of said dispenser.

10. The water treatment system of claim 1 wherein the free sitting bacteria killing chemical comprises solid chlorine tablets.

11. The water treatment system of claim 1 wherein the dispersal valve includes:

a passage for directing a fluid stream through said dispersal valve;

a compartment located in said dispersal valve;

an inlet located in said dispersal valve for directing a fluid mixing stream into said compartment;

an outlet located in said dispersal valve for directing the fluid mixing stream out of said compartment; and a valve located in said dispersal valve for controlling the amount of water directed into the inlet located in said dispersal valve.

12. The chemical dispersant apparatus of claim 10 wherein the dispenser has a top and a bottom with the inlets and outlets there located on the bottom of said dispenser.

13. The chemical dispersant apparatus of claim 11 wherein the dispenser includes limestone.

14. The water treatment system of claim 1 wherein the free-sitting chemical comprises chlorine tablets having an outer dimension only slightly smaller than the second compartment of the dispenser so that the water flowing through the water treatment system is urged to flow along the bottom of the second compartment in the dispenser.

15. The water treatment system of claim 14 wherein the water is maintained at a selected level in the dispersal valve so as to cover the chlorine tablets therein.

16. A water treatment system for killing bacteria in situ and in a main body of water comprising:

a dispersal valve for directing water therethrough; and a mineral dispenser, said mineral dispenser having a first bacteria killing mineral therein selected from the four groups consisting of;

zinc metal particles, uncoated limestone particles and limestone particles at least partially covered with silver chloride;

limestone particles, zinc metal particles and zinc metal particles covered with silver chloride and with an outer protective layer of porous epoxy over the silver chloride;

uncoated limestone particles, limestone particles partially coated with silver chloride and zinc carbonate particles; and uncoated limestone particles and limestone particles at least partially covered with silver chloride.

17. The water treatment system of claim 16 wherein the first bacteria killing mineral in the mineral dispenser includes zinc metal particles.

18. The water treatment system of claim 16 wherein the first bacteria killing mineral in the mineral dispenser includes a zinc containing material selected from the group consisting of zinc carbonate, zinc silicate, zinc sulfate, zinc chloride, zinc oxide, zinc hydroxide, zinc stearate or combinations thereof.

19. The water treatment system of claim 16 wherein the mineral dispenser includes a chamber having a bacteria killing chemical therein.

20. The water treatment system of claim 19 wherein the bacteria killing chemical is chlorine.

* * * * *